US008704002B2

(12) United States Patent
Jagusch et al.

(10) Patent No.: US 8,704,002 B2
(45) Date of Patent: Apr. 22, 2014

(54) PROCESS FOR THE DEHYDRATION OF SUBSTITUTED 4-DIMETHYLAMINO-2-ARYL-BUTAN-2-OL COMPOUNDS AND PROCESS FOR THE PREPARATION OF SUBSTITUTED DIMETHYL-(3-ARYL-BUTYL)-AMINE COMPOUNDS BY HETEROGENEOUS CATALYSIS

(71) Applicant: Gruenenthal GmbH, Aachen (DE)

(72) Inventors: Utz-Peter Jagusch, Aachen (DE); Wolfgang Hoelderich, Frankenthal (DE); Monika Voerckel, Ahrensburg (DE)

(73) Assignee: Grünenthal GmbH, Aachen (DE)

( * ) Notice: Subject to any disclaimer, the term of this patent is extended or adjusted under 35 U.S.C. 154(b) by 0 days.

(21) Appl. No.: 13/667,110

(22) Filed: Nov. 2, 2012

(65) Prior Publication Data

US 2013/0060065 A1    Mar. 7, 2013

Related U.S. Application Data

(63) Continuation of application No. 11/313,937, filed on Dec. 22, 2005, now abandoned, and a continuation of application No. PCT/EP2004/006666, filed on Jun. 21, 2004.

(30) Foreign Application Priority Data

Jun. 23, 2003  (DE) .................................. 10328316

(51) Int. Cl.
*C07C 213/08* (2006.01)
*C07C 217/62* (2006.01)

(52) U.S. Cl.
USPC ............ 564/335; 564/374; 564/383; 564/388

(58) Field of Classification Search
None
See application file for complete search history.

(56) References Cited

U.S. PATENT DOCUMENTS

| | | |
|---|---|---|
| 4,012,456 A | 3/1977 | Chaplits |
| 4,276,195 A | 6/1981 | Verkade |
| 4,889,777 A | 12/1989 | Akuto |
| 5,565,594 A | 10/1996 | Spindler et al. |
| 5,583,241 A | 12/1996 | Spindler |
| 5,783,715 A | 7/1998 | Pugin |
| 5,811,582 A | 9/1998 | Buschmann et al. |
| 6,203,939 B1 | 3/2001 | Wilson |
| 6,248,737 B1 | 6/2001 | Buschmann et al. |
| 6,372,387 B1 | 4/2002 | Kawakami et al. |
| 6,890,959 B2 | 5/2005 | Puetz et al. |
| 7,417,170 B2 | 8/2008 | Hell et al. |
| 7,589,196 B2 | 9/2009 | Pugin et al. |
| 2002/0010178 A1 | 1/2002 | Buschmann et al. |
| 2002/0074972 A1 | 6/2002 | Narang et al. |
| 2004/0106046 A1 | 6/2004 | Inda |
| 2004/0191630 A1 | 9/2004 | Kawamura et al. |
| 2006/0167318 A1 | 7/2006 | Jagusch et al. |
| 2006/0194988 A1 | 8/2006 | Hell et al. |
| 2010/0009916 A1 | 1/2010 | Bokvist et al. |

FOREIGN PATENT DOCUMENTS

| | | |
|---|---|---|
| CA | 2170100 A1 | 8/1996 |
| CN | 1163884 A | 11/1997 |
| DE | 2 254 929 A1 | 5/1973 |
| DE | 107 260 | 7/1974 |
| DE | 124521 | 3/1977 |
| EP | 0 612 758 A1 | 8/1994 |
| EP | 0 646 590 A1 | 4/1995 |
| EP | 0 693 475 A1 | 1/1996 |
| EP | 0 728 768 A2 | 8/1996 |
| EP | 0 729 969 A1 | 9/1996 |
| EP | 0 799 819 A1 | 10/1997 |
| GB | 1 381 755 A | 1/1975 |
| GB | 1 394 542 | 5/1975 |
| JP | 6-90934 B2 | 11/1994 |
| JP | 07-326372 | 12/1995 |
| JP | 11-345629 A | 12/1999 |
| JP | 2002-158039 | 5/2002 |
| JP | 2004-185862 | 7/2004 |
| KR | 1992-0005187 B | 6/1992 |
| KR | 1999-0078427 A | 10/1999 |
| WO | WO 01/49651 A2 | 7/2001 |
| WO | WO 2004/089920 A2 | 10/2004 |
| WO | WO 2004/108658 A1 | 12/2004 |
| WO | WO 2005/000788 A1 | 1/2005 |

OTHER PUBLICATIONS

Bussas et al., "Ene reaction mechanisms. 1. Chirality transfer to the enophile 4-methyl-N-sulfinylbenzenesulfonamide", J. Org. Chem. 1983, vol. 48, No. 17, pp. 2828-2832 (three (3) sheets).
Goodman et al.,"The Pharmacological Basis of Therapeutics, $9^{th}$ Edition, Section II-Drugs Acting at Synaptic and Neuroeffector Junctional Sites", (abstract) p. 1 (one (1) sheet), 2003.
Guczi et al., "New Frontiers in Catalysis—Proceedings of the 10th International Congress on Catalysis, Budapest, Jul. 19-24, 1992", 1993, vol. 75, Elsevier Science Publishers B. V., (table of contents) (twenty-six (26) sheets).
Harmer et al., "Nation Resin-Silica Nao-Composite Solid Acid Catalysts", Green Chemistry, Feb. 8, 2000, pp. 7-14, The Royal Society of Chemistry (eight (8) sheets).
Hoelderich, "New Aspects in the Performance of Heterogeneous Catalysts for Intermediates and Fine Chemicals", Studies in Surface Science and Catalysis, 1988, vol. 41, (abstract), pp. 83-90 (two (2) sheets).

(Continued)

*Primary Examiner* — Yevegeny Valenrod
(74) *Attorney, Agent, or Firm* — Hunton & Williams LLP

(57) ABSTRACT

Process for the preparation of substituted dimethyl-(3-aryl-butyl)-amine compounds. The process comprises dehydration by heterogeneous catalysis of substituted 4-dimethy-lamino-2-aryl-butan-2-ol compounds, to form substituted dimethyl-(3-aryl-but-3-enyl)-amine intermediates, which are then converted by hydrogenation with hydrogen to substituted dimethyl-(3-aryl-butyl)-amine compounds.

6 Claims, No Drawings

(56) References Cited

OTHER PUBLICATIONS

Hoelderich, "Environmentally Benign Manufacturing of Fine and Intermediate Chemicals", Catalysis Today, 2000, vol. 62, (abstract), pp. 115-130 (one (1) sheet).

Hoelderich et al., "Chapter 16 'Zeolites in Organic Syntheses'", Studies in Surface Science and Catalysis, 1991, vol. 58, (abstract), pp. 631-726 (one (1) sheet).

Kozhevnikov, "Heteropoly Acids and Related Compounds as Catalysts for Fine Chemical Synthesis", Catalysis Reviews: Science and Engineering, 1995, vol. 37, No. 2, pp. 311-352 (forty-three (43) sheets).

Meiers, "Direktsynthese von Propylenoxid in Gegenwart von Wasserstoff", 1998, (table of contents) (eight (8) sheets).

Olah et al., "Perfluorinated Resinsulfonic Acid (Nation-H®) Catalysis in Synthesis", Synthesis, Jul. 1986, pp. 513-531 (nineteen (19) sheets).

Sachtler et al., "Zeolite-Supported Transition Metal Catalysts", Advances in Catalysis, 1993, vol. 39, pp. 129-220 (summary) (one (1) sheet).

Song et al., "Sulfated Zirconia-Based Strong Solid-Acid Catalysts: Recent Progress", Catalysis Reviews: Science and Engineering, 1996, vol. 38, No. 3, pp. 329-412, (eighty-five (85) sheets).

Venuto, "Organic Catalysis Over Zeolites: A Perspective on Reaction Paths Within Micropores", Microporous Materials, Jun. 1994, vol. 2, issue 5, (abstract), pp. 297-411 (one (1) sheet).

Schmidle et al, J. Am. Chem. Soc., 1995, 77, 4636-4638.

Yasuda et . (J. Org. Chem, 2001 66, 7741).

Lucke et al. (English translation of DD 12451) 1977.

Tetsuji Kametani et al., "Syntheses of Analgesics. XXVIII, Syntheses of 4-Amino-3-methyl-1,2-diphenyl-2-propionyloxybutane Derivatives" Yakugaku Zhassi, vol. 92, No. 4, 1972, pp. 421-430, XP009074552, Japan p. 424.

Maurilio Tramontini, "Advances in the Chemistry of Mannich Bases", Synthesis, No. 12, 1973, XP002406126, p. 712: table 6.

International Search Report dated Oct. 30, 2007 (Seven (7) pages).

European Search Report dated Nov. 22, 2006 (Seven (7) pages).

Written Opinion of the International Search Authority (Six (6) pages), 2007.

Lubell, W. D. et al., "α-Amino Acids as Chiral Educts for Asymmetric Products. Alkylation of N-Phenylfluorenyl α-Amino Ketones. Synthesis of Optically Pure α-Alkyl Carboxylic Acids", J. Am. Chem. Soc., vol. 110, No. 22, 1988, pp. 7447-7455, XP002419870.

International Preliminary Report on Patentability including English translation (Eleven (11) pages).

PROCESS FOR THE DEHYDRATION OF SUBSTITUTED 4-DIMETHYLAMINO-2-ARYL-BUTAN-2-OL COMPOUNDS AND PROCESS FOR THE PREPARATION OF SUBSTITUTED DIMETHYL-(3-ARYL-BUTYL)-AMINE COMPOUNDS BY HETEROGENEOUS CATALYSIS

CROSS REFERENCE TO RELATED APPLICATIONS

This application is a continuation of application Ser. No. 11/313,937, filed Dec. 22, 2005, which in turn was a continuation of international application no. PCT/EP04/06666, filed Jun. 21, 2004, published in German on Jan. 6, 2005 as WO 2005/000788. Priority is claimed based on Federal Republic of Germany patent application no. DE 103 28 316.1, filed Jun. 23, 2003.

BACKGROUND OF THE INVENTION

The present invention relates to a process for the dehydration of substituted 4-dimethylamino-2-aryl-butan-2-ol compounds and to processes for the preparation of substituted dimethyl-(3-aryl-butyl)-amine compounds by heterogeneous catalysis.

Opioids, for example morphine, have been used in the therapy of pain for many years, although they cause a number of side-effects, for example addiction, dependency, respiratory depression, impaired gastro-intestinal motility and constipation. They can therefore be taken for a prolonged period and in relatively high doses only with particular safety measures (Goodman, Gilman, The Pharmacological Basis of Therapeutics, Pergamon Press, New York 1990).

Because of the high demand for a pain therapy that is satisfactory for the patient, the search for new, highly effective and tolerable pain relievers is the focus of medical research.

With the development of substituted dimethyl-(3-aryl-but-3-enyl)-amine compounds, as are described, for example, in EP 0 799 819, it has been possible to make available new pain relievers that are distinguished by very good effectiveness and that exhibit no side-effects or at least side-effects that are markedly reduced compared with conventional pain relievers.

The preparation of these compounds is carried out by dehydration of appropriately substituted 4-dimethylamino-2-aryl-butan-2-ol compounds which have a tertiary alcohol function, using acid, in particular formic acid or hydrochloric acid. This process has the disadvantage that the acid used for the dehydration must subsequently be separated from the reaction mixture by neutralisation and, optionally, repeated extraction.

The resulting salt can lead to equipment corrosion, and side products such as the waste water has a negative effect on the environment, and the production costs of the process is also high. A further class of active ingredients having excellent analgesic effectiveness and very good tolerability are the substituted dimethyl-(3-aryl-butyl)-amine compounds, which are known inter alia from EP 0 693 475.

The preparation of these pharmaceutical active ingredients is likewise carried out starting from tertiary alcohols, which are first converted into the corresponding chloride compound and then reduced with zinc borohydride, zinc cyanoborohydride or tin cyanoborohydride. This process has the disadvantage that the preparation of the chloride compound is carried out with the use of comparatively aggressive chlorinating agents such as thionyl chloride. Furthermore, the process does not give a satisfactory yield in all cases.

SUMMARY OF THE INVENTION

The object of the present invention was, therefore, to provide a process for removing the tertiary alcohol function from substituted 4-dimethylamino-2-aryl-butan-2-ol compounds, with which process the correspondingly substituted dimethyl-(3-aryl-but-3-enyl)-amine compounds are obtained in good yields under environmentally protective conditions and whereby it is also possible to prepare correspondingly substituted dimethyl-(3-aryl-butyl)-amine compounds in good yields with a simplified procedure.

According to the invention, this object is achieved by the provision of the processes described hereinbelow for the dehydration of substituted 4-dimethylamino-2-aryl-butan-2-ol compounds of the general formula I below and for the preparation of substituted dimethyl-(3-aryl-butyl)-amine compounds of the general formula III below, optionally with isolation of substituted dimethyl-(3-aryl-but-3-enyl) compounds of the general formula II below. The compounds of the general formulae II and III are preferably used as pharmaceutical active ingredients in medicaments and are suitable in particular for controlling pain.

Accordingly, the present invention provides a process for the dehydration of at least one substituted 4-dimethylamino-2-aryl-butan-2-ol compound of the general formula I

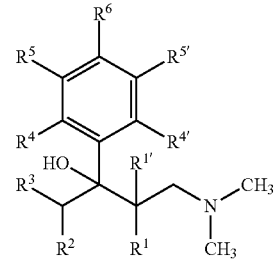

wherein
$R^1$ represents H or $C_{1-5}$-alkyl,
$R^{1'}$ represents H or $C_{1-5}$-alkyl,
$R^2$ represents H or $C_{1-5}$-alkyl,
$R^3$ represents H or $C_{1-5}$-alkyl,
$R^4$, $R^{4'}$, $R^5$, $R^{5'}$, $R^6$, which may be identical or different, each represents H, OH, $C_{1-4}$-alkyl, $OC_{1-4}$-alkyl, partially fluorinated or perfluorinated $C_{1-4}$-alkyl, partially fluorinated or perfluorinated $O-C_{1-4}$-alkyl, $O-(CH_2)_n$-phenyl where n=1, 2 or 3, F, Cl or $OR^8$,
or two adjacent radicals $R^4$ and $R^5$, $R^5$ and $R^6$, $R^6$ and $R^{5'}$ or $R^{5'}$ and $R^{4'}$ represent a group —OCH=CHO—, —CH=C($R^9$)—O—, —CH=C($R^9$)—S— or —CH=CH—C($OR^{10}$) =CH— as part of a ring, with the proviso that the other radicals in each case $R^6$, $R^{5'}$ and $R^{4'}$; $R^4$, $R^{5'}$ and $R^{6'}$; $R^4$, $R^5$ and $R^{4'}$; or $R^4$, $R^5$ and $R^6$ are as defined above,
$R^8$ represents $CO-C_{1-5}$-alkyl, $PO(O-C_{1-4}$-alkyl$)_2$, $CO-C_6H_4-R^{11}$, $CO(O-C_{1-5}$-alkyl), $CO-CHR^{12}-NHR^{13}$, $CO-NH-C_6H_3-(R^{14})_2$ or an unsubstituted or substituted pyridyl, thienyl, thiazoyl or phenyl group,
$R^9$ represents H or $C_{1-4}$-alkyl,
$R^{10}$ represents H or $C_{1-3}$-alkyl,
$R^{11}$ represents $OC(O)-C_{1-3}$-alkyl in the ortho-position or —$CH_2$—N—$(R^{15})_2$ in the meta- or para-position, where $R^{15}$ in each case represents $C_{1-4}$-alkyl or the two radicals $R^{15}$, together with the bridging nitrogen atom, form a 4-morpholino radical,
$R^{12}$ and $R^{13}$, which may be identical or different, each represents H, $C_{1-6}$-alkyl or $C_{3-8}$-cycloalkyl,
or $R^{12}$ and $R^{13}$ together represent $-(CH_2)_{3-8}$ as part of a ring,
$R^{14}$ represents H, OH, $C_{1-7}$-alkyl, partially fluorinated or perfluorinated $C_{1-7}$-alkyl, $OC_{1-7}$-alkyl, phenyl, O-aryl, F or Cl, with the proviso that the radicals $R^{14}$ are identical or different, in each case in the form of one of their pure stereoisomers, in particular enantiomers or diastereoisomers, of their racemates or in the form of a mixture of stereoisomers, in particular of enantiomers or diastereoisomers, in any desired mixing ratio, or in each case in the form of a physiologically acceptable salt, or in each case in the form of a solvate,
according to which process at least one compound of the general formula I is dehydrated with heterogeneous catalysis to form, as end product, a substituted dimethyl-(3-aryl-but-3-enyl)-amine compound of the general formula II

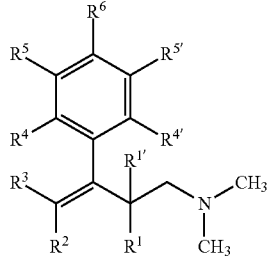

II wherein $R^1$, $R^{1'}$, $R^2$, $R^3$, $R^4$, $R^{4'}$, $R^5$, $R^{5'}$ and $R^6$ are each as defined above, in each case optionally in the form of one of their pure stereoisomers, in particular enantiomers or diastereoisomers, of their racemates or in the form of a mixture of stereoisomers, in particular of enantiomers or diastereoisomers, in any desired mixing ratio, or in each case in the form of a physiologically acceptable salt, or in each case in the form of a solvate, and the end product is optionally isolated and optionally purified.

The substituted dimethyl-(3-aryl-but-3-enyl)-amine compounds of the general formula II obtained by the above-described process can be reacted according to conventional processes known to the person skilled in the art to form substituted dimethyl-(3-aryl-butyl)-amine compounds of the general formula III below.

Accordingly, the present invention further provides a process for the preparation of at least one substituted dimethyl-(3-aryl-butyl)-amine compound of the general formula III

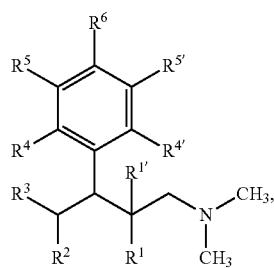

III wherein the radicals $R^1$, $R^{1'}$, $R^2$, $R^3$, $R^4$, $R^{4'}$, $R^5$, $R^{5'}$ and $R^6$ are each as defined above, in each case in the form of one of their pure stereoisomers, in particular enantiomers or diastereoisomers, of their racemates or in the form of a mixture of stereoisomers, in particular of enantiomers or diastereoisomers, in any desired mixing ratio, or in each case in the form of a physiologically acceptable salt, or in each case in the form of a solvate, according to which process at least one substituted 4-dimethylamino-2-aryl-butan-2-ol compound of the general formula I

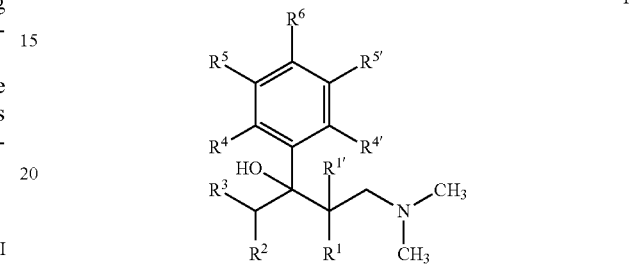

I wherein the radicals $R^1$, $R^{1'}$, $R^2$, $R^3$, $R^4$, $R^{4'}$, $R^5$, $R^{5'}$ and $R^6$ are each as defined above, in each case in the form of one of their pure stereoisomers, in particular enantiomers or diastereoisomers, of their racemates or in the form of a mixture of stereoisomers, in particular of enantiomers or diastereoisomers, in any desired mixing ratio, or in each case in the form of a physiologically acceptable salt, or in each case in the form of a solvate, is dehydrated with heterogeneous catalysis to form, as intermediate, a substituted dimethyl-(3-aryl-but-3-enyl)-amine compound of the general formula II

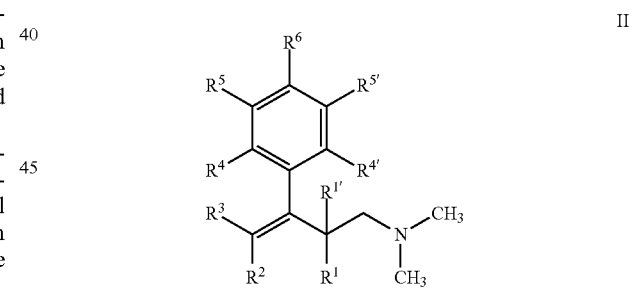

II wherein the radicals $R^1$, $R^{1'}$, $R^2$, $R^3$, $R^4$, $R^{4'}$, $R^5$, $R^{5'}$ and $R^6$ are each as defined above, in each case optionally in the form of one of their pure stereoisomers, in particular enantiomers or diastereoisomers, of their racemates or in the form of a mixture of stereoisomers, in particular of enantiomers or diastereoisomers, in any desired mixing ratio, or in each case in the form of a physiologically acceptable salt, or in each case in the form of a solvate, the intermediate is optionally isolated, is optionally purified and is reacted to form, as end product, a substituted dimethyl-(3-aryl-butyl)-amine compound of the general formula III.

In the processes according to the invention preference is given to the use of substituted 4-dimethylamino-2-aryl-butan-2-ol compounds of the general formula Ia

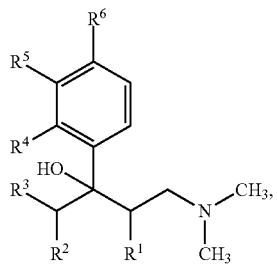

Ia wherein
$R^1$ is $C_{1-5}$-alkyl,
$R^2$ represents H or $C_{1-5}$-alkyl,
$R^3$ represents H or $C_{1-5}$-alkyl,
$R^4$ is H, OH, $C_{1-4}$-alkyl, O—$C_{1-4}$-alkyl, O-benzyl, $CF_3$, O—$CF_3$, Cl, F or $OR^8$,
$R^5$ is H, OH, $C_{1-4}$-alkyl, O—$C_{1-4}$-alkyl, O-benzyl, $CHF_2$, $CF_3$, O—$CF_3$, Cl, F or $OR^8$,
$R^6$ represents H, OH, $C_{1-4}$-alkyl, O—$C_{1-4}$-alkyl, O-benzyl, $CF_3$, O—$CF_3$, Cl, F or $OR^8$, with the proviso that two of the radicals $R^4$, $R^5$ and $R^6$ are H;
or $R^4$ and $R^5$ together represent a group —CH=C($R^9$)—O— or —CH=C($R^9$)—S— as part of a ring, and $R^6$ is H; or $R^5$ and $R^6$ together represent a group —CH=CH—C($OR^{10}$)=CH— as part of a ring, and that $R^4$ is H,
$R^8$ represents CO—$C_{1-5}$-alkyl, PO(O—$C_{1-4}$-alkyl)$_2$, CO—$C_6H_4$—$R_{11}$, CO(O—$C_{1-5}$-alkyl), CO—$CHR^{12}$—$NHR^{13}$, CO—NH—$C_6H_3$—$(R^{14})_2$ or an unsubstituted or substituted pyridyl, thienyl, thiazoyl or phenyl group,
$R^9$ represents H or $C_{1-4}$-alkyl,
$R^{10}$ represents H or $C_{1-3}$-alkyl,
$R^{11}$ represents OC(O)—$C_{1-3}$-alkyl in the ortho-position or —$CH_2$—N—$(R^{15})_2$ in the meta- or para-position, where $R^{15}$ is $C_{1-4}$-alkyl or the two radicals $R^{15}$, together with the bridging nitrogen atom, form a 4-morpholino radical,
$R^{12}$ and $R^{13}$ are identical or different and represent H, $C_{1-6}$-alkyl or $C_{3-8}$-cycloalkyl, or $R^{12}$ and $R^{13}$ together represent a group —$(CH_2)_{3-8}$— as part of a ring,
$R^{14}$ represents H, OH, $C_{1-7}$-alkyl, O—$C_{1-7}$-alkyl, phenyl, O-aryl, $CF_3$, Cl or F, with the proviso that the two radicals $R^{14}$ are identical or different.

In the processes according to the invention particular preference is given to the use of substituted 4-dimethylamino-2-aryl-butan-2-ol compounds of the general formula Ia wherein
$R^1$ is $C_{1-3}$-alkyl,
$R^2$ is H or $C_{1-3}$-alkyl,
$R^3$ is H or $C_{1-3}$-alkyl,
$R^4$ is H, OH, Cl, F or $OR^8$,
$R^5$ is H, OH, $C_{1-4}$-alkyl, O—$C_{1-4}$-alkyl, O-benzyl, $CHF_2$, $CF_3$, Cl, F or $OR^8$,
and $R^6$ is H, OH, O—$C_{1-4}$-alkyl, O-benzyl, $CF_3$, Cl, F or $OR^8$,
with the proviso that two of the radicals $R^4$, $R^5$ and $R^6$ are H,
or $R^4$ and $R^5$ together represent a group —CH=C($R^9$)—O— or —CH=C($R^9$)—S—, in each case as part of a ring, and $R^6$ is H; or $R^5$ and $R^6$ together represent a group —CH=CH—C($OR^{10}$)=CH— as part of a ring, and that $R^4$ is H,
$R^8$ to $R^{10}$ are as defined above.

In the processes according to the invention very particular preference is given to the use of substituted 4-dimethylamino-2-aryl-butan-2-ol compounds of the general formula Ia wherein $R^1$ is $CH_3$ or $C_3H_7$,
$R^2$ is H, $CH_3$ or $CH_2CH_3$,
$R^3$ is H, $CH_3$ or $CH_2CH_3$,
$R^4$ is H or OH,
$R^5$ is H, OH, $OCH_3$, $CHF_2$ or $OR^8$,
$R^6$ is H, OH or $CF_3$,
with the proviso that two radicals $R^4$, $R^5$ or $R^6$ are H; or $R^4$ and $R^5$ together represent a group —CH=C($CH_3$)—S— as part of a ring, and $R^6$ is H; or $R^5$ and $R^6$ together represent —CH=CH—C(OH)=CH— as part of a ring, and $R^4$ is H, $R^8$ represents CO—$C_6H_4$—$R^{11}$ and $R^{11}$ represents —OC(O)—$C_{1-3}$-alkyl in the ortho-position.

In the processes according to the invention there are most preferably used 1-dimethylamino-3-(3-methoxy-phenyl)-2-methyl-pentan-3-ol in particular in the form of its isolated enantiomers or diastereoisomers or in the form of mixtures of its stereoisomers, the first-mentioned alcohol compounds being reacted by the process according to the invention for the preparation of substituted dimethyl-(3-aryl-butyl)-amine compounds of the general formula III to form 3-(3-methoxy-phenyl)-2-methyl-pentyl-dimethylamine and the last-mentioned alcohol compounds being reacted to form 3-(3-methoxy-phenyl)-2-methyl-pentyl-dimethylamine, in particular in the form of its isolated enantiomers or diastereoisomers or in the form of mixtures of its stereoisomers.

The substituted 4-dimethylamino-2-aryl-butan-2-ol compounds can be prepared by conventional processes known to the person ordinarily skilled in the art, as described, for example, in EP 0 693 475 and EP 0 799 819, the corresponding descriptions of which are incorporated herein by reference and form part of the disclosure.

The substituted dimethyl-(3-aryl-but-3-enyl)-amine compounds obtained by dehydration of substituted 4-dimethylamino-2-aryl-butan-2-ol compounds are, where appropriate, usually in the form of a mixture of their stereoisomers. These can be separated from one another by conventional methods known to the person ordinarily skilled in the art, for example by means of chromatographic methods.

The reaction of the substituted dimethyl-(3-aryl-but-3-enyl)-amine compounds of the general formula II to form substituted dimethyl-(3-aryl-butyl)-amine compounds of the general formula III optionally likewise leads to a mixture of different stereoisomers, which can be separated from one another by conventional methods known to the person ordinarily skilled in the art. Examples which may be mentioned include chromatographic separation processes, in particular liquid chromatography processes under normal pressure or under elevated pressure, preferably MPLC and HPLC processes, as well as processes of fractional crystallisation. It is thereby possible in particular to separate from one another individual enantiomers, e.g. by means of HPLC on chiral phase or by means of crystallisation with chiral acids, for example (+)-tartaric acid, (−)-tartaric acid or (+)-10-camphorsulfonic acid, diastereoisomeric salts that have formed.

The person ordinarily skilled in the art will understand that the use of differently substituted 4-dimethylamino-2-aryl-butan-2-ol compounds of the general formula I in the processes according to the invention leads to correspondingly substituted dimethyl-(3-aryl-but-3-enyl) compounds of the general formula II or to correspondingly substituted dimethyl-(3-aryl-butyl)-amine compounds of the general formula III.

The substituted 4-dimethylamino-2-aryl-butan-2-ol compounds of the general formula I, like the substituted dimethyl-(3-aryl-but-3-enyl)-amine compounds of the general formula II, can be used in the processes according to the invention in each case both in the form of their bases, their acids and in each case in the form of their salts or in each case in the form of corresponding solvates, preferably hydrates. Of course, it is also possible to use mixtures of two or more of the above-mentioned compounds.

When at least one substituted 4-dimethylamino-2-aryl-butan-2-ol compound of the general formula I or at least one substituted dimethyl-(3-aryl-but-3-enyl)-amine compound of the general formula II is reacted by the process according to the invention in the form of a salt, the salt can preferably be selected from the group consisting of chloride, bromide, sulfate, sulfonate, phosphate, tartrate, teoclate, embonate, formate, acetate, propionate, benzoate, oxalate, succinate, citrate, diclofenacate, naproxenate, salicylate, acetylsalicylate, glutamate, fumarate, asp artate, glutarate, stearate, butyrate, malonate, lactate, mesylate, saccharinate, cyclamate and acesulfamate, particularly preferably from the group consisting of chloride, sulfate, saccharinate, teoclate, embonate, diclofenacate, naproxenate, ibuprofenate and salicylate.

The salts are usually in the form of a corresponding acid addition salt, for example in the form of the hydrochloride.

When the substituted dimethyl-(3-aryl-but-3-enyl)-amine compounds of the general formula II or the substituted dimethyl-(3-aryl-butyl)-amine compounds of the general formula III are obtained by the processes according to the invention in the form of their bases, they can be converted into the corresponding salts, preferably into one of the salts listed above, by conventional processes known to the person ordinarily skilled in the art.

Heterogeneous catalysis within the context of the present invention means that the catalysts used in the processes according to the invention are in each case present in the solid state of aggregation.

The term catalyst within the context of the present invention includes both catalytically active materials themselves and inert materials that are provided with a catalytically active material. Accordingly, the catalytically active material can, for example, be applied to an inert carrier or can be present in a mixture with an inert material. There come into consideration as inert carrier or inert material, for example, carbon and other materials known to the person skilled in the art.

The substituted 4-dimethylamino-2-aryl-butan-2-ol components or the substituted dimethyl-(3-aryl-but-3-enyl)-amine components used in the processes according to the invention are preferably in liquid phase and to that end are preferably mixed with or dissolved in a reaction medium that is liquid under the particular reaction conditions.

Examples of suitable reaction media are water or organic liquids such as halogenated organic compounds, alcohols or ketones, preferably dichloromethane, chloroform, toluene or methanol, particularly preferably acetone or especially ethanol. Of course, it is also possible to use mixtures or multiphase systems comprising two or more of the above-mentioned liquids in the processes according to the invention. A reaction in supercritical $CO_2$ as solvent is also possible.

The dehydration of the substituted 4-dimethylamino-2-aryl-butan-2-ol compounds of the general formula I is preferably carried out in the presence of at least one acidic catalyst and/or at least one basic catalyst, particularly preferably in the presence of at least one acidic catalyst. It is also possible to use catalysts that have been provided with both acidic and basic properties.

Suitable acidic and/or basic catalysts can preferably be selected from the group consisting of ion-exchange resins, zeolites, heteropoly acids, phosphates, sulfates and optionally mixed metal oxides.

The dehydration is preferably carried out in the presence of at least one acidic catalyst, which can preferably be selected from the group consisting of ion-exchange resins, zeolites, heteropoly acids, phosphates, sulfates and optionally mixed metal oxides.

Suitable catalysts and their preparation are known per se to the person skilled in the art, for example from Venuto, P. B., Microporous Mater., 1994, 2, 297; Hölderich, W. F., van Bekkum, H., Stud. Surf. Sci. Catal., 1991, 58, 631, Hölderich, W. F., Proceedings of the 10th International Congress on Catalysis, 1992, Budapest, Guczi, L. et al. (editors), "New Frontiers in Catalysis", 1993, Elsevier Science Publishers, Kozhenikov, I. V., Catal. Rev. Sci. Eng., 1995, 37, 311, Song, X., Sayari, A., Catal. Rev. Sci. Eng., 1996, 38, 329. The corresponding literature descriptions are incorporated herein by reference and form part of the disclosure.

There are suitable for the dehydration in particular those ion-exchange resins that carry sulfonic acid groups.

Preference is given to ion-exchange resins based on tetrafluoroethylene/perfluorovinyl ether copolymers, optionally in the form of their silica nanocomposites, as are described, for example, in the literature publications of Olah et al. Synthesis, 1996, 513-531 and Harmer et al. Green Chemistry, 2000, 7-14, the corresponding descriptions of which are incorporated herein by reference and form part of the disclosure.

Corresponding products are available commercially, for example under the trade name Nafion®, and can also be used in that form in the processes according to the invention.

Preference is further given to ion-exchange resins based on styrene/divinylbenzene copolymers, which can be prepared by conventional processes known to the person skilled in the art.

There come into consideration for the dehydration particularly preferably sulfonic-acid-group-carrying ion-exchange resins based on styrene/divinylbenzene copolymers, as are marketed, for example, under the trade name Amberlyst® by Rohm & Haas and which can also be used as such in the processes according to the invention. These ion-exchange resins are distinguished in particular by their stability towards water and alcohols, even at elevated temperatures, for example from 130 to 160° C.

The degree of crosslinking and the structure of these ion-exchange resins can vary. For example, mention may be made of macroporous ion-exchange resins having heterogeneous pore diameter distribution, isoporous ion-exchange resins having virtually uniform pore diameter distribution, or gel-like ion-exchange resins having no or virtually no pores. The macroporous resins in particular can be used with particular advantage for heterogeneous catalysis in the liquid phase.

Particularly suitable macroporous resins having a mean pore diameter of from about 20 to about 30 nm and a minimum concentration of active groups of from about 4.70 to about 5.45 equivalents per kg of resin are available commercially under the trade names Amberlyst® 15, Amberlyst® 35 and Amberlyst® 36 and accordingly can also be used in the processes according to the invention.

It is likewise preferred to carry out the dehydration in the presence of an acidic catalyst based on metal oxides such as, $SiO_2$, $Al_2O_3$, $TiO_2$, $Nb_2O_5$, $B_2O_3$ or based on mixed metal oxides such as, $Al_2O_3/SiO_2$ or $Al_2O_3/B_2O_3$.

The reaction parameters for the processes according to the invention, for example, pressure, temperature or reaction time, can vary over a wide range.

Preferably, the temperature during these reactions is in each case from about 20 to about 250° C., particularly preferably from about 50 to about 180° C. and very particularly preferably from about 100 to about 160° C.

Both reactions can be carried out at reduced pressure, at normal pressure or at elevated pressure, preferably in the range from about 0.01 to about 300 bar. It is particularly preferred to carry out the reactions under pressure in a range from about 2 to about 10 bar, in particular from about 4 to about 8 bar.

The reaction time can vary in dependence on various parameters, for example, temperature, pressure, nature of the compound to be reacted or the properties of the catalyst, and can be determined for the process in question by the person skilled in the art using preliminary tests.

The ratio of catalyst and compound to be reacted is preferably in the range from about 1:200 to about 1:1, in particular from about 1:4 to about 1:2.

After the dehydration, the catalyst can be separated from the reaction mixture in a simple manner, preferably by filtration. The particular substituted dimethyl-(3-aryl-but-3-enyl)-amine compound of the general formula II obtained as intermediate or end product can be isolated and/or purified by conventional methods known to the person skilled in the art.

The further reaction of the dimethyl-(3-aryl-but-3-enyl)-amine compounds of the general formula II obtained as intermediate can preferably likewise be carried out with heterogeneous catalysis.

In a preferred embodiment of the process according to the invention, the reaction of the substituted dimethyl-(3-aryl-but-3-enyl)-amine compound of the general formula II obtained as intermediate is carried out by heterogeneously catalysed hydrogenation with hydrogen. The hydrogen is preferably in gaseous form, although it is also possible for at least part of it to be dissolved in a liquid phase.

The reaction of the dimethyl-(3-aryl-but-3-enyl)-amine compounds of the general formula II obtained as intermediate with heterogeneous catalysis is preferably carried out in the presence of at least one catalyst that contains one or more transition metals, and optionally in the presence of at least one of the catalysts used above for the dehydration. Alternatively, it is also possible for this reaction to be carried out in the presence of at least one of the polyfunctionalized, preferably bifunctionalized, catalysts described hereinbelow.

In a preferred embodiment of the process according to the invention for the preparation of substituted dimethyl-(3-aryl-butyl)-amine compounds of the general formula III, the dehydration to form the intermediate and its reaction or purification and/or isolation to form the end product are preferably carried out in the presence of at least one polyfunctionalized, preferably bifunctionalized, catalyst.

According to the invention, bi- or poly-functionalized catalysts are understood as being those catalysts that have two or more different functionalities and therefore are able to accelerate two or more different reactions, preferably at least the dehydration and the subsequent reaction of the intermediate so obtained.

Preference is given to bifunctional catalysts that are acidic and/or basic, preferably acidic, and contain at least one transition metal.

Such bifunctionalized catalysts are particularly preferably derived from one of the, catalysts mentioned above preferably acidic, for the dehydration.

When one of the catalysts used in the processes according to the invention contains one or more transition metals, these metals can preferably be selected from the group consisting of Cu, Ag, Au, Zn, Cd, Hg, V, Nb, Ta, Cr, Mo, W, Fe, Ru, Os, Co, Rh, Ir, Ni, Pd, and Pt, particularly preferably from the group consisting of Ru, Rh, Pd, Os, Ir and Pt, and very particularly preferably from the group consisting of Pd, Ru, Pt and Ir. Palladium is most preferred.

The corresponding catalysts can preferably contain one or more of the above-mentioned transition metals in the same or different oxidation states. It may also be preferable for the corresponding catalysts to contain one or more of the above-mentioned transition metals in two or more different oxidation states.

The preparation of catalysts doped with transition metals can be carried out by conventional processes known to the person ordinarily skilled in the art.

The preparation of correspondingly bifunctionalized catalysts can likewise be carried out by conventional methods known to the person skilled in the art, for example by partially loading an ion exchanger with transition metal ions or by impregnation with solutions containing transition metal salts, as described, for example, in Sachtler et al., Advances in Catalysis, 1993, 39, 129. The corresponding literature description is incorporated herein by reference and forms part of the disclosure.

It has further been found that the hydrogenation of at least one substituted dimethyl-(3-aryl-but-3-enyl)-amine compound of the general formula II with hydrogen to form at least one substituted dimethyl-(3-aryl-butyl)-amine compound of the general formula III proceeds particularly advantageously when it is carried out in the presence of a catalyst mixture or in the presence of a polyfunctionalized, preferably bifunctionalized, catalyst.

Accordingly, the present invention further provides a process for the preparation of at least one substituted dimethyl-(3-aryl-butyl)-amine compound of the general formula III

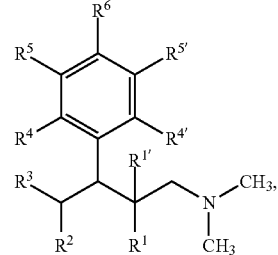

III wherein the radicals $R^1$, $R^{1'}$, $R^2$, $R^3$, $R^4$, $R^{4'}$, $R^5$, $R^{5'}$ and $R^6$ are as defined above, in each case in the form of one of their pure stereoisomers, in particular enantiomers or diastereoisomers, of their racemates or in the form of a mixture of stereoisomers, in particular of enantiomers or diastereoisomers, in any desired mixing ratio, or in each case in the form of a physiologically acceptable salt, or in each case in the form of a solvate, characterized in that at least one substituted dimethyl-(3-aryl-but-3-enyl)-amine compound of the general formula II

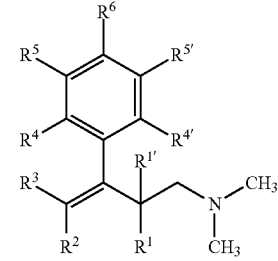

II wherein the radicals $R^1$, $R^{1'}$, $R^2$, $R^3$, $R^4$, $R^{4'}$, $R^5$, $R^{5'}$ and $R^6$ are each as defined above, in each case in the form of one of their pure stereoisomers, in particular enantiomers or diastereoisomers, of their racemates or in the form of a mixture of stereoisomers, in particular of enantiomers or diastereoisomers, in any desired mixing ratio, or in each case in the form of a physiologically acceptable salt, or in each case in the form of a solvate, is reacted to form a compound of the general formula III as end product by hydrogenation with hydrogen with heterogeneous catalysis in the presence of a mixture comprising at least one of the catalysts mentioned above for the dehydration and at least one catalyst containing one or more transition metals, or in the presence of at least one of the bifunctionalized catalysts mentioned above.

The process according to the invention is particularly suitable for preparing a mixture of (−)-(2R,3R)-[3-(3-methoxy-phenyl)-2-methyl-pentyl]-dimethylamine and (−)-(2R,3S)-[3-(3-methoxy-phenyl)-2-methyl-pentyl]dimethylamine from (−)-(2S,3S)-1-dimethylamino-3-(3-methoxy-phenyl)-2-methyl-pentan-3-ol.

The reaction parameters for the processes according to the invention, such as, for example, pressure, temperature or reaction time, can vary over a wide range both in the dehydration of the substituted 4-dimethylamino-2-aryl-butan-2-ol compounds of the general formula I and in the reaction of the substituted dimethyl-(3-aryl-but-3-enyl) compounds of the general formula II.

Preferably, the temperature during these reactions is in each case from 20 to 250° C., particularly preferably from about 50 to about 180° C. and very particularly preferably from about 100 to about 160° C.

Both reactions can be carried out at reduced pressure, at normal pressure or at elevated pressure, preferably in the range from about 0.01 to about 300 bar. It is particularly preferred to carry out the reactions under pressure in a range from about 2 to about 10 bar, in particular from about 4 to about 10 bar.

The reaction time can vary in dependence on various parameters, such as, for example, temperature, pressure, nature of the compound to be reacted or the properties of the catalyst, and can be determined for the process in question by the person skilled in the art using preliminary tests.

The continuous removal of samples in order to monitor the reaction, for example by means of gas chromatography methods, is also possible, optionally in combination with regulation of the corresponding process parameters.

The amount of the catalyst(s) used depends on various factors, such as, the ratio of the catalytically active component to any inert material present, or the nature of the surface of the catalyst. The optimal amount of catalyst for a particular reaction can be determined by the person skilled in the art using preliminary tests.

For the dehydration and hydrogenation in the presence of bifunctionalized ion-exchange resins based on styrene/divinylbenzene copolymers, which carry sulfonic acid groups and have been provided with palladium in an amount of from about 0.1 to about 10 wt. %, preferably from about 0.3 to about 3 wt. %, particularly preferably from about 0.5 to about 2 wt. %, in each case based on the total weight of the catalyst, the catalyst and the compound to be reacted can preferably be used in a ratio of from about 1:200 to about 1:1, particularly preferably from about 1:4 to about 1:2.

The processes according to the invention can each be carried out discontinuously (batchwise) or continuously, preferably with the discontinuous procedure.

Many reactors are suitable for the discontinuous procedure of the present invention, for example, a slurry reactor, and for the continuous procedure a fixed-bed reactor or loop reactor.

The dehydration of substituted 4-dimethylamino-2-aryl-butan-2-ol compounds of the general formula I, and optionally the subsequent reaction of the resulting substituted dimethyl-(3-aryl-but-3-enyl)-amine compounds of the general formula II, is possible by the process according to the invention in a good yield and with very good purities.

In comparison to the conventional preparation processes, chlorination of the alcohol with aggressive reagents, or the working-up and disposal of comparatively large amounts of acid, are not necessary for the process of the present invention.

Because the dehydration and the subsequent reaction of the dehydrated compound to prepare substituted dimethyl-(3-aryl-butyl)-amine compounds of the general formula III, preferably by hydrogenation, are carried out in a common process step, the environmental balance and the duration of this process, and accordingly its economy, can also be improved still further.

The solid catalysts used according to the invention can additionally be separated from the reaction mixture in a simple manner, optionally regenerated and used again.

The invention is explained hereinbelow by means of Examples. These explanations are given only by way of example and do not limit the general inventive concept.

EXAMPLES

Example 1

Preparation of the Bifunctional Catalyst

1a)

In a round-bottomed flask, 2 g of a sulfonic-acid-group-carrying ion-exchange resin based on a styrene/divinylbenzene copolymer having a divinylbenzene content of 20 wt. %, based on the total weight of the resin, a mean pore diameter of 25 nm and a minimum concentration of active groups of 4.70 equivalents per kg of resin (Amberlyst® 15, Fluka, Switzerland) were suspended in 20 ml of water. 0.3 ml of a palladium tetramine dinitrate hydrate solution having a palladium content of 69.5 mg/ml was then added, and stirring was carried out for 24 hours at a temperature of 80° C. To prepare the palladium(II) tetramine nitrate hydrate complex solution, 10 g of palladium(II) nitrate dihydrate (Fluka) were added to 400 g of ammonia solution (25 wt. % in water) and the mixture so obtained was stirred for 3 days at 50° C. The undesired solid was then separated off by filtration, and the palladium content was determined by ICP-AES, as described in R. Meiers, Dissertation RWTH-Aachen, Shaker-Verlag (1998). The corresponding description is incorporated herein by reference and forms part of the disclosure. The catalyst so obtained was then filtered off, washed with water and dried for 3-4 hours at 120° C. under a medium-high vacuum. The finished product has a Pd content of 1 wt. %.

1b)

In a round-bottomed flask, 2 g of a sulfonic-acid-group-carrying ion-exchange resin based on a styrene/divinylbenzene copolymer having a divinylbenzene content of 12 wt. %, based on the total weight of the resin, a mean pore diameter of 20 nm and a minimum concentration of active groups of 5.45 equivalents per kg of resin (Amberlyst® 36, Fluka, Switzerland) were suspended in 20 ml of water. 0.3 ml of a palladium tetramine dinitrate hydrate solution, prepared according to Example 1a, having a palladium content of 69.5 mg/ml was then added, and stirring was carried out for 24 hours at a temperature of 80° C. The catalyst so obtained was then filtered off, washed with water and dried for 3-4 hours at 120° C. under a medium-high vacuum. The finished product has a Pd content of 1 wt. %.

Example 2

Synthesis of (Z;E)-(S)-[3-(3-methoxy-phenyl)-2-methyl-pent-3-enyl]-dimethyl-amine; hydrochloride (2) from (−)-(2S,3S)-1-dimethylamino-3-(3-methoxy-phenyl)-2-methyl-pentan-3-ol; hydrochloride (1)

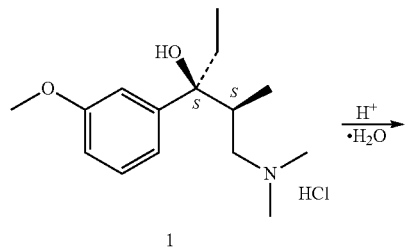

1.0 g (3.4 mmol.) of (−)-(2S,3S)-1-dimethylamino-3-(3-methoxy-phenyl)-2-methyl-pentan-3-ol; hydrochloride (1) and 0.5 g of a sulfonic-acid-group-carrying ion-exchange resin based on a styrene/divinylbenzene copolymer having a divinylbenzene content of 20 wt. %, based on the total weight of the resin, a mean pore diameter of 25 nm and a minimum concentration of active groups of 4.70 equivalents per kg of resin (Amberlyst® 15, Fluka, Switzerland) were placed in a 75 ml stainless steel autoclave. After addition of 15 ml of freshly distilled ethanol, the reaction mixture was stirred for 4 hours at 150° C. in the closed system (at an overall pressure of up to 8 bar). After cooling to room temperature (about 20-25° C.), the catalyst was filtered out. A sample of the filtrate so obtained was taken and analyzed by gas chromatography using a 50 m SE-54 column from Chrompack.

More than 98% of (−)-(2S,3S)-1-dimethylamino-3-(3-methoxy-phenyl)-2-methyl-pentan-3-ol; hydrochloride (1) were converted.

The yield of (Z;E)-(S)-[3-(3-methoxy-phenyl)-2-methyl-pent-3-enyl]-dimethyl-amine; hydrochloride (2) was 92-95% with a Z:E ratio of 70:30.

Example 3

Synthesis of (−)-(2R,3R)-[3-(3-methoxy-phenyl)-2-methyl-pentyl]-dimethyl-amine; hydrochloride (3a) and (−)-(2R,3S)-[3-(3-methoxy-phenyl)-2-methyl-pentyl]-dimethyl-amine; hydrochloride (3b) from (Z)—(S)-[3-(3-methoxy-phenyl)-2-methyl-pent-3-enyl]-dimethyl-amine; hydrochloride (2)

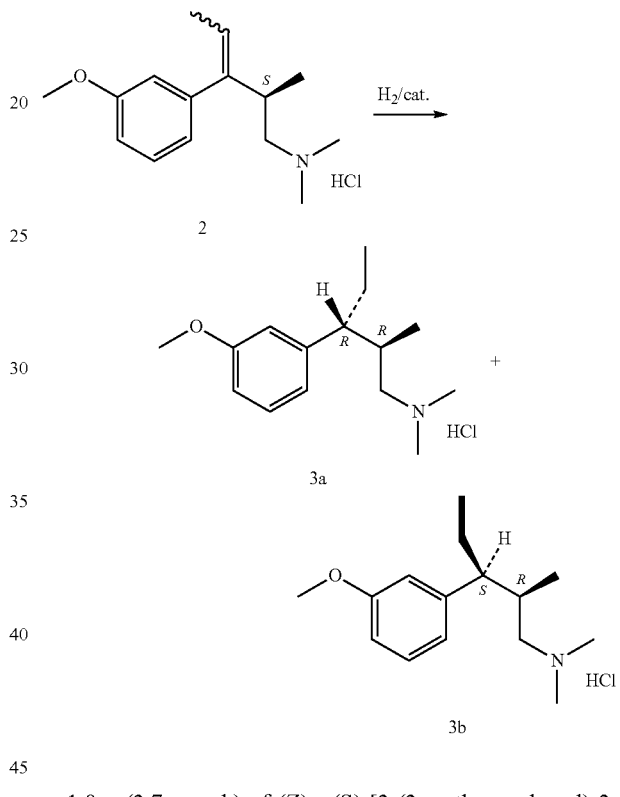

1.0 g (3.7 mmol.) of (Z)—(S)-[3-(3-methoxy-phenyl)-2-methyl-pent-3-enyl]-dimethyl-amine; hydrochloride (2) and 0.5 g of the catalyst obtained according to Example 1a were placed in a 75 ml stainless steel autoclave. The autoclave was evacuated under a medium-high vacuum and then gassed with argon. Under an argon atmosphere, 15 ml of freshly distilled ethanol were added. A hydrogen pressure of 4 bar was then applied at room temperature, and the reaction mixture was stirred for 4 hours at 150° C. (overall pressure at 150° C. up to 12 bar). After cooling to room temperature, the excess hydrogen was let off and the catalyst was filtered off. A sample of the filtrate was taken and analyzed by gas chromatography using a 50 m SE-54 column from Chrompack.

More than 98% of (Z)—(S)-[3-(3-methoxy-phenyl)-2-methyl-pent-3-enyl]-dimethyl-amine; hydrochloride were converted.

The yield of [3-(3-methoxy-phenyl)-2-methyl-pentyl]-dimethyl-amine; hydrochloride (3) was >96% with a ratio of the enantiomer (−)-(2R,3R) to the diastereoisomer (−)-(2R,3S) of 76:24. The (−)-(2R,3R) enantiomer is preferably used as an active ingredient in medicaments.

Example 4

Direct synthesis of (−)-(2R,3R)-[3-(3-methoxy-phenyl)-2-methyl-pentyl]-dimethyl-amine; hydrochloride from (−)-(2S,3S)-1-dimethylamino-3-(3-methoxy-phenyl)-2-methyl-pentan-3-ol; hydrochloride 4a 1.0 g (3.4 mmol.) of (−)-(2S,3S)-1-dimethylamino-3-(3-methoxy-phenyl)-2-methyl-pentan-3-ol; hydrochloride and 0.5 g of the catalyst obtained according to Example 1a were placed in a 75 ml stainless steel autoclave. The autoclave was evacuated under a medium-high vacuum and then gassed with argon. Under an argon atmosphere, 15 ml of freshly distilled ethanol were added. A hydrogen pressure of 4 bar was then applied at room temperature, and the reaction mixture was stirred for 4 hours at 150° C. (overall pressure at 150° C. up to 12 bar). After cooling to room temperature, the excess hydrogen was let off and the catalyst was filtered off. A sample of the filtrate was taken and analyzed by gas chromatography using a 50 m SE-54 column from Chrompack.

For isolation of the crystalline product mixture, the ethanol was first removed in a rotary evaporator and then the crude product so obtained was recrystallized from heptane:tetrahydrofuran in a ratio of 1:1 (volume/volume), yielding colourless crystals which were again analyzed by means of gas chromatography.

The conversion of (Z)—(S)-[3-(3-methoxy-phenyl)-2-methyl-pent-3-enyl]-dimethyl-amine; hydrochloride 2 was more than 98%.

The yield of [3-(3-methoxy-phenyl)-2-methyl-pentyl]-dimethyl-amine; hydrochloride (3) was 91% (of theory) with a diastereoisomeric ratio of the compound having the (R,R) configuration, which is preferably used as a pharmaceutical active ingredient in a medicament, to the compound having the (S,R) configuration of 64:36.

4b)

The preparation was carried out analogously to Example 4a), the catalyst obtained according to Example 1b) being used instead of the catalyst obtained according to Example 1a).

Over 95% of (Z)—(S)-[3-(3-methoxy-phenyl)-2-methyl-pent-3-enyl]-dimethyl-amine; hydrochloride were converted.

The yield of [3-(3-methoxy-phenyl)-2-methyl-pentyl]-dimethyl-amine; hydrochloride was 90%, with a ratio of the compound having the (R,R) configuration to the diastereoisomer (S,R) of 61:39.

The invention claimed is:

1. A method for converting a compound of Formula I

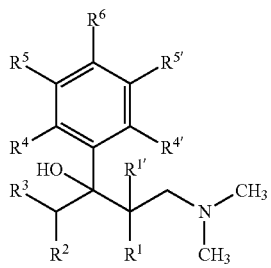

I wherein
$R^1$ represents H or $C_{1-5}$-alkyl,
$R^{1'}$ represents H or $C_{1-5}$-alkyl,
$R^2$ represents H or $C_{1-5}$-alkyl,
$R^3$ represents H or $C_{1-5}$-alkyl,
$R^4$, $R^{4'}$, $R^5$, $R^{5'}$, $R^6$, which may be identical or different, each represents H, OH, $C_{1-4}$-alkyl, $OC_{1-4}$-alkyl, partially fluorinated or perfluorinated $C_{1-4}$-alkyl, partially fluorinated or perfluorinated O—$C_{1-4}$-alkyl, O—$(CH_2)_n$-phenyl where n=1, 2 or 3, F, Cl or $OR^8$,
or two adjacent radicals $R^4$ and $R^5$, $R^5$ and $R^6$, $R^6$ and $R^{5'}$ or $R^{5'}$ and $R^{4'}$ represent a group —OCH═CHO—, —CH═C($R^9$)—O—, —CH═C($R^9$)—S— or —CH═CH—C($OR^{10}$)═CH— as part of a ring, with the proviso that the other radicals in each case $R^6$, $R^{5'}$ and $R^{4'}$; $R^4$, $R^{5'}$ and $R^{6'}$; $R^4$, $R^5$ and $R^{4'}$ or $R^4$, $R^5$ and $R^6$ are as defined above,
$R^8$ represents CO—$C_{1-5}$-alkyl, PO(O—$C_{1-4}$-alkyl)$_2$, CO—$C_6H_4$—$R^{11}$, CO(O—$C_{1-5}$-alkyl), CO—$CHR^{12}$—$NHR^{13}$, CO—NH—$C_6H_3$—$(R^{14})_2$ or an unsubstituted or substituted pyridyl, thienyl, thiazoyl or phenyl group,
$R^9$ represents H or $C_{1-4}$-alkyl,
$R^{10}$ represents H or $C_{1-3}$-alkyl,
$R^{11}$ represents OC(O)—$C_{1-3}$-alkyl in the ortho-position or —$CH_2$—N—$(R_{15})_2$ in the meta- or para-position, where $R^{15}$ in each case represents $C_{1-4}$-alkyl or the two radicals $R^{15}$, together with the bridging nitrogen atom, form a 4-morpholino radical,
$R^{12}$ and $R^{13}$, which may be identical or different, each represents H, $C_{1-6}$-alkyl or $C_{3-8}$-cycloalkyl, or $R^{12}$ and $R^{13}$ together represent —$(CH_2)_{3-8}$ as part of a ring,
$R^{14}$ represents H, OH, $C_{1-7}$-alkyl, partially fluorinated or perfluorinated $C_{1-7}$-alkyl, $OC_{1-7}$-alkyl, phenyl, O-aryl, F or Cl, with the proviso that the radicals $R^{14}$ are identical or different,
wherein in each case the compound of Formula I is in the form of one of its pure stereoisomers, a racemate, or in the form of a mixture of stereoisomers, in any desired mixing ratio, or in each case in the form of a physiologically acceptable salt, or in each case in the form of a solvate, comprising dehydrating the compound of Formula I via catalysis carried out in the presence of a polyfunctional heterogeneous catalyst to form a compound of Formula II

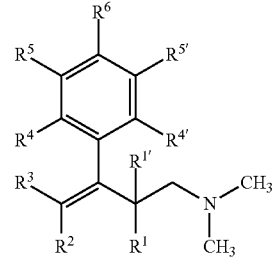

II wherein $R^1$, $R^{1'}$, $R^2$, $R^3$, $R^4$, $R^{4'}$, $R^5$, $R^{5'}$ and $R^6$ are as defined above, in each case in the form of one of its pure stereoisomers, a racemate, or a mixture of stereoisomers, in any desired mixing ratio, or in each case in the form of a physiologically acceptable salt, or in each case in the form of a solvate.

2. The method according to claim 1, wherein the stereoisomer of the compound of Formula I or Formula II is an enantiomer or a diastereoisomer.

3. The method according to claim 1, wherein the polyfunctional heterogeneous catalyst is at least one acidic catalyst comprising ion-exchange resins, zeolites, heteropoly acids, phosphates, and sulfates, or at least one basic catalyst.

4. The method according to claim 3, wherein the acidic catalyst further comprises at least one metal oxide including $SiO_2$, $Al_2O_3$, $TiO_2$, $Nb_2O_5$, $B_2O_3$, a mixture of $Nb_2O_5$ and $B_2O_3$, a mixture of $Al_2O_3$ and $SiO_2$, or a mixture of $Al_2O_3$ and $B_2O_3$, wherein said metal oxide is mixed with the component selected from the group consisting of ion-exchange resins, zeolites, heteropoly acids, phosphates, or sulfates.

5. The method according to claim 4, wherein the ion-exchange resins comprise sulfonic acid groups.

6. The method according to claim 4, wherein the ion-exchange resins are based on at least one tetrafluoroethylene/perfluorovinyl ether copolymer or at least one styrene/divinylbenzene copolymer.

* * * * *